United States Patent [19]

Denney et al.

[11] 4,383,043
[45] May 10, 1983

[54] MAGNESIUM ASSAY WITH CALMAGITE OR ERIOCHROME BLACK T REAGENTS

[75] Inventors: Jerry W. Denney, Carmel; Robert L. Long, Indianapolis, both of Ind.

[73] Assignee: American Monitor Corporation, Indianapolis, Ind.

[21] Appl. No.: 282,721

[22] Filed: Jul. 13, 1981

[51] Int. Cl.$^3$ .............................................. G01N 33/52
[52] U.S. Cl. ...................................... 436/74; 422/61; 436/79
[58] Field of Search .......................... 23/230 B, 230 R; 252/408; 436/74, 79; 422/61

[56] References Cited

U.S. PATENT DOCUMENTS

| | | | |
|---|---|---|---|
| 3,754,864 | 8/1973 | Gindler | 23/230 B |
| 3,754,865 | 8/1973 | Gindler | 23/230 B |
| 3,798,000 | 3/1974 | Helger | 23/230 B |
| 4,205,955 | 6/1980 | Sloat | 23/230 R |

OTHER PUBLICATIONS

S. A. Cohen, Clin. Chem., 26(6), 783 (1980).

*Primary Examiner*—Sidney Marantz
*Attorney, Agent, or Firm*—Robert A. Spray

[57] ABSTRACT

A colorimetric assay method and stabilized working reagents for the determination of magnesium in which an alkaline reagent containing a dye to complex magnesium reacts directly with the sample, requiring no protein-removal steps and no addition of substances to artificially correct for absorption differences of the metallized and free dye due to the presence of protein. The dye is either Calmagite or Eriochrome Black T. The reagent is buffered so that the pH is greater than about 9.0; the relative Van Slyke buffer value $\beta'$ of the reagent is greater than 1.

38 Claims, No Drawings

MAGNESIUM ASSAY WITH CALMAGITE OR ERIOCHROME BLACK T REAGENTS

BACKGROUND OF THE INVENTION

Role of Magnesium and Vital Need for Accurate and Reliable Magnesium Measurements Magnesium is extremely significant in human physiology. It is one of the most abundant cations in the body and, next to potassium, it is the most prevalent intracellular ion. Magnesium in its ionic form is essential to many physiological processes. It plays a vital and major role in carbohydrate and lipid metabolism by serving as an activator of adenosine triphosphate (ATP) in the transfer of energy rich phosphate. It is also essential as an activating ion for many enzymes involved in lipid, carbohydrate and protein metabolism. In muscle tissue, magnesium has a significant influence on neuromuscular apparatus. Magnesium ions are also essential for the preservation of the macromolecular structure of DNA, RNA and ribosomes; and in addition they play a vital part in bone formation and the maintenance of osmotic pressure.

The amount of magnesium in the body is particularly significant. Decreased levels of magnesium in the body produce muscle irritability which, if not corrected, can result in tetany (prolonged involuntary muscle spasms), which is clinically indistinguishable from that caused by decreased calcium levels, and convulsions. On the other hand, increased levels of magnesium have a curare-like effect, resulting in a loss of deep tendon reflexes, a loss of touch, temperature and pain sensation, respiratory failure, and cardiac arrest.

Because of the vitally important roles magnesium plays in the normal functioning of life processes, it has long been recognized that it is necessary to be able to accurately and reliably measure magnesium levels in the body in order to aid the physician in diagnosis and treatment. In addition, it is correspondingly necessary that such results are able to be produced urgently in response to an emergency or STAT request from a physician. The ever-increasing recognition by clinicians of the need for frequent determinations of serum magnesium levels requires that the procedure desirably be capable of being performed by automated means. Of further importance, since blood samples obtained from pediatric or geriatric patients are usually very small, it is necessary that methods used for accurately determining magnesium levels desirably utilize no more than an extremely small sample volume.

Prior Art and Its Failures and Disadvantages

For many years, physicians regarded the determination of magnesium levels in serum or plasma to be of limited value due to the numerous errors to which the earlier techniques were subject, causing an unreliability which the prior art sought to avoid by several different approaches. In fact, even though improvements in certain respects were achieved, the great variety of methods still in current use for measuring the amount of magnesium in biological fluids in testament to the fact that none of them is completely satisfactory, even after long years of attempted improvement. Most are tedious, inaccurate or rely upon expensive instrumentation of limited usefulness which is not likely to be available except in the largest and most highly sophisticated clinical laboratories. Many difficulties have hindered the development of accurate and precise methods for the determination of magnesium, among which are the nonspecific nature of its precipitation reactions, the liability to interference from other ions, and the relatively low intensity of its spectral lines.

The oldest of the methods for measuring magnesium levels in biological fluids, but one which is still occasionally used, is an indirect method which involves precipitation of the magnesium as magnesium ammonium phosphate. The phosphorus in the precipitate is then quantified by a variety of means, among which are photometric measurement as molybdenum blue or as the molybdivanadate complex. Following determination of the phosphate content, magnesium concentration is mathematically calculated.

But these indirect methods have disadvantages. In these indirect precipitation methods, phosphate contamination of the precipitate must be eliminated without loss of the precipitate itself; however, interferring calcium must first be removed, and the procedures are all cumbersome, difficult to perform, time-consuming, and largely abandoned due to lack of accuracy.

Another group of indirect methods involves precipitation of magnesium with 8-hydroxyquinoline. The precipitate can then be quantitated by titrimetry, colorimetry, flame photometry or fluorometry. Here again, however, calcium interference must be eliminated, and the procedures suffer the drawbacks of being tedious, time-consuming, very subject to manipulative errors, or requiring special instrumentation.

The search for less tedious procedures more suitable for clinical use led to the application of the color reaction of magnesium with the dye Titan Yellow (Clayton Yellow), first described by Kolthoff in 1927.[1] The colloidal or unevenly dispersed nature of the magnesium hydroxide-dye lake introduces obvious limitations to the method. Although variations of the original method are still in use today, they still suffer major drawbacks, including the requirement of the preparation of a protein-free filtrate, limited sensitivity, only limited adherence to Beer's law, color instability, erratic results which do not agree with those obtained by atomic absorption, and significant interference from calcium gluconate, which is frequently administered in clinical situations where magnesium levels are being monitored.

Flame photometry has been advocated, but a number of technical problems and limitations have discouraged the use of flame photometry as a practical or accurate clinical method for the measurement of magnesium. The light emitted by magnesium is of very low intensity, thereby requiring a highly sensitive photodetector system and relatively large slit widths, both of which intensify the effects of intrinsic interferences from specific emission bands of the usual combustible gases and interference from other anions such as sodium and potassium.

Various titrimetric techniques have also been used for the determination of magnesium based on titrations with the complexing agent EDTA (ethylenediaminetetraacetic acid) using a variety of indicators, one of the most popular being Eriochrome Black T (3-hydroxy-4-[(1-hydroxy-2-naphthalenyl)azo]-7-nitro-1-naphthalenesulfonic acid monosodium salt). Since calcium is also chelated by EDTA, its concentration must be established, either by a second titration or other means, and the magnesium level then calculated as the difference. Thus, the indirectness of this procedure means that the chances for cumulative errors are high, and it is difficult to produce measurements with much precision or accuracy due to the largely subjective measurement of the color change at endpoint, which may be variable according to the rate of titration, or may be gradual in the presence of protein or moderately high levels of phosphate, such as are common in urine or in serum in renal failure.

Techniques that measure the fluorescence of a chelate of magnesium and a fluorescent indicator (commonly 8-hydroxyquinoline) are also used for the determination of magnesium. However, interference from numerous drugs or medications which also fluoresce, and interference due to nonspecific random quenching of fluorescence are serious drawbacks to these methods, for they can easily cause inaccurate results to be observed.

Atomic absorption is perhaps the most accurate, even if not a practical or convenient, means of determining magnesium levels in biological fluids. When light from a lamp containing a magnesium electrode passes through a flame which contains vapors of a fluid whose magnesium content is to be measured, the amount of light that is absorbed by the flame is directly proportional to the magnesium concentration. The intensity of the emerging light beam passes via a monochromator to a photomultiplier detector. Although this method is today generally considered to be the reference method for magnesium determinations, there are serious limitations to its routine use in the clinical laboratory. The cost of the instrumentation alone is prohibitive in most clinical or hospital laboratories; a number of instrument problems remain to be solved, such as lamp stability and lamp life; highly skilled or specially trained personnel are required to operate the instrumentation; and due to sample size requirements, the method is not practical for pediatric or neonatal specimens. Furthermore, the method is not practical when urgent results are required as in the case of emergency requests from physicians.

Recently, direct colorimetric dye-complexing methods using the indicators Magon, methylthymol blue, and Calmagite have become increasingly popular. The use of Magon was first reported by Mann et al.[2] and by Bohoun.[3] Currently used modifications of these original methods are relatively fast and simple to perform; however, the methods suffer from significant interference due to lipemia, bilirubin, and hemolysis, and more importantly, the methods have been shown to produce erroneous results in the presence of citrate, which is a common constituent of intravenous fluids and blood used for transfusions. Thus those critically ill patients who might be in greatest peril because of their serum magnesium levels, and who are the persons most likely to receive intravenous fluids or blood are most likely to suffer the life-threatening event of a false analytical result in measuring their blood serum magnesium levels.

Another method which employed Eriochrome Black T was that of Gitelman.[4] This prior art procedure was an automated method; however, among other drawbacks, it required the removal of protein from the sample prior to reaction with the dye, and the working reagent used was stable for only a few days. The Gitelman prior art used inverse colorimetry; however, its use appears to have been subsequently abandoned by those skilled in the art.

As an additional desire for the improvement of magnesium assays, those skilled in the art have historically sought ways to perform assays directly on serum or other appropriate samples, rather than to perform cumbersome and time-consuming protein removal or other pre-treatment steps, which also can consume a large quantity of sample as well as introduce errors into the assay.

The direct dye-complexing methods which might be considered to be the most closely related of the prior art to the present method are those employing the dyestuff Calmagite (3-hydroxy-4-[(2-hydroxy-5-methylphenyl)azo]-1-naphthalenesulfonic acid). These methods involve the fact that Calmagite is known to become "metallized" by reaction with several metal ions such as calcium, magnesium, iron, and copper to form a metallized complex. The prior art has included EGTA (ethyleneglycol-bis[$\beta$-aminoethyl ether]-N,N'-tetraacetic acid) and potassium cyanide to mask the metallizing of Calmagite by metals other than magnesium, such as iron, copper, and calcium which are normally found in blood serum and which might otherwise interfere in the assay. Thus magnesium is the primary metal in blood serum which metallizes Calmagite in the prior art procedures. Unmetallized Calmagite is blue in an alkaline medium, and when metallized or bound with magnesium forms a reddish-colored complex. The blue, unmetallized Calmagite compound has a different spectral absorbance peak than does the metallized or magnesium bound compound.

The prior art method of Gindler[5] and Gindler et al.[6] incorporates those known properties of Calmagite and its reaction with metal ions and also those known properties of EGTA and potassium cyanide to mask the metallizing of Calmagite by iron, copper, and calcium normally found in blood; but the Gindler art also teaches that protein in serum produces a spectral shift in the absorbance of free and metallized Calmagite, thus introducing errors when a non-protein solution is used for calibration. The unmetallized Calmagite, which is blue in an alkaline medium (having an optimal absorbance between 600 and 650 nm) binds with magnesium to form a reddish-colored complex having an optimal absorbance of about 535 nm. The prior art teaches that the absorbance measurement at 532 nm is proportional to the amount of magnesium and thus serves as a quantitation of the amount of magnesium.

The Gindler prior art teaches that the spectral absorbance peak of the reddish-colored metallized dye is shifted in the presence of protein from 535 to 540 nm. In order to overcome this alleged interference from protein, selected micelle-forming protective colloids and detergents are added to the reaction mixture to mimic the interference from protein. These added substances, the prior art asserts, achieve spectral correlation between protein-containing and aqueous samples. Specifically, the prior art teaches that the absorbance peak of both protein-containing and aqueous samples is shifted to 545 nm when a micelle-forming protective colloid is added. Although this prior art method does achieve certain advantages over the earlier art, there remain or are created certain drawbacks, as now discussed.

The working reagent mixture of the Gindler et al. prior art is stable for no longer than several hours,[6] thereby requiring not only the labor, cost and effort of reagent preparation every day, but the disposal and costly wastage of unused, prepared working reagent at the end of the day, and inaccuracy or unworkability if attempted to be used after that short stability period.

The addition of a micelle-forming protective colloid and detergents is believed, according to the novel concepts of the present invention, to unnecessarily complicate the formulation and possibly introduces adverse properties to the assay. The prior art teaches a measurement at 532 nm, which is close to the absorbance of chromogenic substances such as hemoglobin, bilirubin, and lipemia which may be present in certain patients' serum. Consequently, when measurements are made at 532 nm on patient's serum which contains hemoglobin, bilirubin or which is lipemic, the absorbance of these substances is likely to be wrongly determined as being due to the presence of magnesium. Therefore, the analyst could be led to report a higher level of magnesium to be present in the patient's blood serum than is actually present, thereby potentially leading the physician to a mistaken diagnosis or improper treatment of the patient, with obviously dangerous or other disadvantageous results.

Also, the normal range of serum magnesium levels is a very narrow one, i.e., ranging from only 1.7 to 2.1 milliequivalents per liter of serum,[7] and it is readily apparent that a clinically useful assay for magnesium must provide sufficient accuracy and sensitivity to accurately distinguish between normal and pathological levels. The limited sensitivity of the prior art methods for magnesium measurement diminish the likelihood of precise measurements of serum magnesium levels.

SUMMARY OF THE INVENTION

Achievements of the Present Invention

From the foregoing discussion of prior art methods, it is apparent that, of the large variety that are still in current use, none is without serious drawbacks and disadvantages. Accordingly, it is an object of the present invention to overcome several serious failures of the prior art.

One objective of the present invention is to provide a rapid assay so that the response time required for urgently needed results is reduced to a minimum, thereby eliminating unnecessary delay in providing treatment for a patient. In the present invention, reaction time is reduced to less than one minute. Further benefits of a rapid assay are the easy adaptability of the method to a variety of high-speed automated instrumentation that is being used in ever-increasing numbers in clinical laboratories today.

A further objective of the present invention is to provide increased reagent stability. The present invention achieves far greater reagent stability than the most closely related of the prior art, even when utilized as a single working reagent. In the present invention, stability of a single working reagent is achieved for periods of several weeks to several months or longer, depending on the particular agent used to complex magnesium, as contrasted to the stability of a few hours common to the prior art. This achievement of the present invention in itself can account for the savings of much time and labor required from daily reagent preparation and for the saving of quantities of unused reagent which must otherwise be discarded at the end of each working day.

It is a further objective of the present invention to provide an assay method which can provide greater accuracy of results and an extended linear range over that achieved by the prior art. When the present invention is employed in a preferred mode wherein the measurement of the loss in absorbance of the unmetallized dye is used to determine the amount of magnesium present in a serum sample, more accurate results are obtained due to the virtual elimination of interference from spectral absorption due to the presence of hemoglobin, bilirubin or lipemia. Moreover, the present invention has doubled the range over which accurate results are obtained as compared to the closest of the prior art. Other achievements and advantages of the present invention will become apparent upon reading the description contained herein.

DESCRIPTION OF THE PRESENT INVENTION

The present invention utilizes an agent (Calmagite or Eriochrome Black T) to complex magnesium, an agent (cyanide) for complexing heavy metals, and an agent (EGTA) to complex calcium. Although certain of these agents were utilized in prior art procedures, the present invention departs from the teachings of the prior art in several ways.

First, no micelle-forming protective colloid is needed to be used in the composition of the reagent. Also, it has been discovered that when the reagent is alkalinized to the proper pH (about pH 11) with a buffer of sufficient strength, a simplified and improved reagent for the measurement of magnesium is derived.

More particularly, the concepts of the present invention seem to avoid a primary difficulty asserted by Gindler, i.e., a difference in absorption spectrum depending upon whether or not protein is present in the sample being quantified; and thus the present invention avoids the need of the micelle-forming protective colloid which is quite basic to the Gindler art, a particularly surprising result in view of the fact that the Gindler text expressly asserts the need of the micelle-forming protective colloid even though it expressly notes that a buffer might desirably be used in the assay.

Further, it has been discovered that when a reagent prepared with Calmagite is used in an assay method in which the step of measuring the loss in absorbance at about 620 nm of the blue, unmetallized Calmagite, in contrast to the prior art's step of measurement at 532 nm of the reddish-colored complex, even greater improvement over prior art methods is obtained. Likewise, a reagent prepared with Eriochrome Black T has been discovered to be useful in a direct serum reaction method, requiring no protein precipitation or removal, by measuring the loss of color at about 640-680 nm. Color loss measurements as described above are particularly useful in minimizing interferences from hemolysis, lipemia and bilirubin.

Moreover, although Eriochrome Black T has previously been used to measure magnesium as an indicator in a titration method or in reactions on samples in which protein has been removed, its use in a direct method is believed to be a novel and useful improvement.

It has also been discovered that when the working reagent is made to contain about 5 percent dimethylsulfoxide (DMSO), the properties of the reagents for use in a magnesium assay are even further improved over prior art reagents, particularly in the significant extension of the stability of the working reagent. It has been found that the presence of a combination of DMSO and desirably at least one non-ionic surfactant increases and enhances the stability of the alkaline Calmagite reagent, and also reduces interference due to the presence of gross turbidity (as seen in certain types of pathological specimens), such interference being most noticeable when an assay procedure is employed wherein the absorbance of the bound magnesium-Calmagite complex is measured, that wavelength being also close to the one wherein endogenous serum lipids and other turbidity also absorb light.

When the concepts of the present invention are optimally applied in a magnesium assay, the goals of the present invention are met; that is, the assay is extremely rapid, the range over which the reaction provides a linear response has been greatly extended, interference from endogenous serum chromogens has been minimized, and a single working reagent with greatly enhanced stability has been achieved, all without the necessity of complicating the formula and reaction with substances to ostensibly or artificially shift the spectral characteristics of the dye complex.

The present invention departs significantly from the teachings of the prior art with respect to the use of buffers, particularly as herein described.

The Gindler prior art[5] does not teach one of ordinary skill in the art how to select the proper type of buffer to be used, but instead teaches the selection of what the present concepts indicate is the least desirable buffer. In fact, in the Gindler preferred embodiment, potassium hydroxide (KOH) is termed a "buffer". It is well known to those of ordinary skill in the art that KOH is a very weak buffer at a pH of about 12. Thus, in choosing buffers, one of ordinary skill would be led by Gindler to choose a weak buffer; and in prior art subsequent to Gindler, that indeed has been the situation, as illustrated by the post-Gindler work of Wong,[8] which uncritically uses KOH. By contrast, it is a specific teaching of the present invention that stronger buffers are to be desired and are useful, in combination with other novel concepts of the present invention, in improving the quality of magnesium assays.

By implication, the lexicon of the Gindler teaching defines a buffer to be a compound such as KOH, which is characterized as a buffer in the Gindler embodiment. No other clarification is given. Since KOH would not in ordinary chemical parlance be called a buffer, or even a typical buffer, one of ordinary skill in the art would be led to use the word "buffer" in the Gindler teaching as defining a compound such as KOH.

A buffer is defined in Willard[9] as "a solution which maintains a nearly constant pH value despite the addition of substantial quantities of acid or base." Potassium hydroxide can hardly be called a buffer by this definition. When acid is added to a solution of KOH, the hydrogen ion concentration increases in direct proportion to the amount of acid added; in other words, for every mole of added acid, there is a corresponding and proportional change in hydrogen ion concentration, to a very close approximation. That is not true of a solution of a buffer according to the Willard definition above, wherein the hydrogen ion concentration, or pH, does not change in direct proportion to the amount of acid added, but instead resists the change and lags to a great degree.

A number of common buffers known to be useful for buffering in the alkaline pH range were found to be useful in the present invention. These include monoethanolamine, diethanolamine, triethanolamine, diethylamine, 3-(cyclohexylamino)-propanesulfonic acid (CAPS), and 2-amino-2-methyl-1-propanol, all of which have strong buffering capacity in the alkaline pH range, quite in contrast to the KOH used by Gindler. An indication of the greatly increased buffer strength of the present invention over the prior art Gindler method is shown by the fact that 23 milliequivalents of hydrochloric acid per liter were found to cause a change in pH to 9.0 when titrating working reagent made according to the Gindler prior art, whereas a much greater amount of acid, 328 milliequivalents per liter, was found to be required to bring the working reagent made according to the teaching of the present invention (specifically that of Example I below) to the same pH. Thus the reagents of the present invention have more than 14 times the buffer strength of the prior art reagent.

The selection of pH 9.0 was based on the ionization constants of Calmagite. Any pH below 9.0 would be approaching the area where a significantly interferring amount of non-ionized dye would exist, and it is well known to those skilled in the art that it is the monovalent form of the dye that reactively binds with magnesium.

A convenient and useful designation concerning the buffering capacity of a buffer solution, and thus a useful designation for comparing and contrasting different buffer solutions, is the designation of the buffer's Van Slyke buffer value $\beta$.[9] The Van Slyke buffer value $\beta$ indicates the resistance of a buffer to change in pH upon addition of an acid or base, and is defined as shown by the ratio $\Delta B/\Delta pH$, where B is an increment of completely dissociated base (or acid) in gram-equivalents per liter that is required to produce a unit change in pH within the solution.

The most meaningful and easily understood relationship, however, may not be the $\beta$ value but the actual resistance to pH change of the reagent of the present invention relative to that of the Gindler prior art reagent. Correspondingly, it seems convenient to use what may be referred to as the relative Van Slyke buffer value, or $\beta'$, which is the buffer value obtained when titrating a working reagent to pH 9.0 relative to that of similarly titrated Gindler reagent. Thus $\beta'$ is defined herein as the number obtained by dividing the amount of acid required for such pH change by the amount of acid required when similarly titrating the working reagent of the Gindler prior art.

Concepts of the present invention show that the buffer's relative Van Slyke buffer value $\beta'$ should be greater than 1, and desirably at least 10. This is significantly different than the $\beta'$ buffer value of the only "buffer" (KOH) taught by Gindler and by the prior art subsequent to Gindler who use the Gindler method.

The spectra of the metallized and free dye in the present invention are not influenced by the presence of protein. Samples containing protein can be assayed using either a protein or a non-protein standard solution for calibration. The Gindler prior art teaches that the addition of a particularly selected micelle-forming protective colloid must be included to avoid spectral absorbance differences between such solutions. However, no such colloid is included in the present invention, and an assay employing the present invention can be calibrated with either aqueous or protein-based materials with no resulting difference in spectral absorbance peaks.

Although the present invention can be practiced by additions of the desired ingredients to the sample individually or in the form of one or more reagent combinations, it is customary and convenient for laboratory or other analytical personnel to use pre-formulated compositions, or reagents, which are generally known as "kits", and which are available on a commercial basis from various manufacturers. A kit may contain one or more pre-formulated reagents and appropriate calibration and quality control materials, or the kit may be in the form of one or more pre-formulated reagents packaged individually or in bulk form for a specific intended use.

With respect to the present invention, it is desirable that the kit contain two separate pre-formulated reagents, one containing the Calmagite or Eriochrome Black T dye and the other containing the buffering or alkalinizing agent. Both reagents may also contain other desired ingredients such as masking agents, stabilizing agents, antimicrobial agents, and so forth.

PREFERRED EMBODIMENTS

The specific embodiments of the present invention detailed herein are provided to enable an analyst skilled in the art to understand and produce reagents and to perform an assay according to the inventive concepts and achievements of the present invention.

EXAMPLE I

Reagents

Dye Reagent:

A stock dye reagent was prepared by making a solution of the following composition:
 82 mg/liter EGTA
 100 ml/liter dimethylsulfoxide
 131 mg/liter Calmagite
 40 gm/liter sodium chloride
The pH of this solution was adjusted to 7.0 with hydrochloric acid.

Buffer Reagent:

A stock buffer reagent was prepared by making a solution of the following composition:
 110 gm/liter diethanolamine
 0.5 gm/liter sodium cyanide
 10 ml/liter Brij ®—35 (25 percent solution)
 6 ml/liter Triton ®X—100
The pH of this solution was adjusted to 12.0 with sodium hydroxide.

Alkaline Calmagite Working Reagent:

This reagent was prepared by mixing together equal volumes of the stock dye reagent and stock buffer reagent. It was found to remain stable for at least three months at room temperature, with a projected stability of up to about a year. The $\beta'$ was found to be 14.3.

Assay Procedure 1

In a reaction vessel or test tube, 5 ml of the alkaline Calmagite working reagent and 50 microliters of the sample to be assayed were mixed together. For calibration, a sample of known magnesium concentration was similarly treated. After one minute, the absorbance of the reaction mixtures was measured at 547 nm, the instrument having been set to zero absorbance with alkaline Calmagite working reagent.

Assay Procedure 2

Using an automated chemical analyzer capable of performing mathematical comparisons involving a color loss, in this example the American Monitor KDA ® analyzer, an amount of sample to be assayed and alkaline Calmagite working reagent were mixed together in the preferred ratio of 1 part sample to 100 parts alkaline Calmagite reagent. The amount of resultant loss in color at 620 nm was measured and compared to the loss observed with a calibrator of known magnesium concentration.

EXAMPLE II

Reagents

Dye Reagent:

A stock dye reagent was prepared by making a solution of the following composition:
 75 mg/liter Eriochrome Black T
 83 mg/liter EGTA
 100 ml/liter dimethylsulfoxide
 40 gm/liter sodium chloride
 10 ml/liter Brij ®-35 (25 percent solution)
 6 ml/liter Triton ® X-100
The pH of this solution was adjusted to 6.0 with hydrochloric acid.

Buffer Reagent:

A stock buffer reagent was prepared by making a solution of the following composition:
 110 gm/liter diethanolamine
 0.5 gm/liter sodium cyanide
The pH of this solution was adjusted to 12.0 with sodium hydroxide.

Alkaline Eriochrome Black T Working Reagent:

This reagent was prepared by mixing together equal volumes of the stock dye reagent and the buffer reagent. It was found to remain stable for several months at room temperature, and the $\beta'$ was found to be 12.8.

Assay Procedure 1

In a reaction vessel or test tube, 5 ml of the alkaline Eriochrome Black T working reagent and 20 microliters of the sample to be assayed were mixed together. For calibration, a sample of known magnesium concentration was similarly treated. After one minute, the absorbance of the reaction mixture was measured at 570 nm, the instrument having been set to zero absorbance with alkaline Eriochrome Black T working reagent.

Assay Procedure 2

An amount of sample to be assayed and alkaline Eriochrome Black T reagent were mixed together in the preferred ratio of 1 part sample to 250 parts alkaline Eriochrome Black T reagent. The amount of resultant loss in color at 650 nm was measured and compared to the loss observed with a calibrator of known magnesium concentration.

EXAMPLE III

Reagents

Dye Reagent:

A stock dye reagent was prepared by making a solution of the following composition:
 82 mg/liter EGTA
 100 ml/liter dimethylsulfoxide
 131 mg/liter Calmagite
 40 g/liter sodium chloride
 10 ml/liter Brij ®-35 (25 percent solution)
 6 ml/liter Triton ® X-100
The pH of this solution was adjusted to 7.0 with hydrochloric acid.

Buffer Reagent:

A stock buffer reagent was prepared by making a solution of the following composition:
55 gm/liter CAPS
0.5 gm/liter sodium cyanide The pH of this solution was adjusted to 11.0 with sodium hydroxide.

Alkaline Calmagite Working Reagent:

This reagent was prepared by mixing together equal volumes of the stock dye reagent and stock buffer reagent. It was found to remain stable for at least three months at room temperature, and the $\beta'$ was found to be 3.3.

Assay Procedures

The assay procedures as described in Example I were used.

While the above examples are illustrative, it will be recognized by one skilled in the art that certain modifications may be made without departing from the inventive concepts as set forth herein.

For example, the amount of dimethylsulfoxide and/or surfactants may be altered (or they may even be eliminated entirely) without loss of the usefulness of the reagent composition in an assay for magnesium, although at the sacrifice of the prolonged reagent stability which is achieved by their presence, and also at the expense of the freedom from interference from gross turbidity in serum specimens.

Other modifications to the foregoing embodiments may also be made without departing from the inventive concepts. For example, a number of common buffers known to be useful in the alkaline pH range may be employed, such as monoethanolamine, diethanolamine, triethanolamine, diethylamine, CAPS, and 2-amino-2-methyl-1-propanol. In general, it will be apparent to one skilled in the art that the most useful buffers are those with pKa values in the area of 8 or above; and the buffer used should be one which does not compete with the dye for the binding of magnesium and should not itself have color or absorb light at the wavelengths used in the assay.

Likewise, other wavelengths for absorption measurements close to those used in the embodiments can give adequate utility in the assay, and certain changes can be made to accommodate the specific requirements of the equipment being used. Moreover, the concepts of the present invention may also be employed by one skilled in the art in a test means wherein the color change is measured using reflectance spectroscopy.

Further, it will be obvious to one skilled in the art that a number of detergents known to improve the spectral or optical clarity of serum in alkaline aqueous solution could be used. The detergents chosen should not complex magnesium or produce color with the unmetallized dye.

Finally, Calmagite or Eriochrome Black T-type dyes with molecular structural differences which do not affect their basic properties as employed in the present invention are also within the inventive concepts of the present invention.

REFERENCES

1. Kolthoff, J. M.: Biochem. Z. 185:344–348 (1927).
2. Mann, C. K. and Yoe, J. H.: Anal. Chem. 28:202–205 (1956).
3. Bohoun, C.: Clin. Chim. Acta 7:811–817 (1962).
4. Gitelman, H. J., Hurt, C., and Lutwak, L.: Anal. Biochem 14:106–120 (1966).
5. Gindler, E. M., U.S. Pat. No. 3,754,864, issued Aug. 28, 1973.
6. Gindler, E. M. and Heth, D. A.: Clin. Chem. 17:662 (1971).
7. Weissman, N. and Pileggi, V. J. in Clinical Chemistry: Principles and Technics, 2nd Ed., R. J. Henry, Ed., Harper and Row, New York (1974), p. 678.
8. Wong, H. K. C.: Clin. Chem. 21:169 (1975).
9. Willard, H. H., et al.: Instrumental Methods of Analysis, 5th Ed., D. Van Nostrand, New York, (1974) p. 586.

What is claimed is:

1. A reagent for the determination of magnesium, comprising Calmagite and a strong buffer such that the pH of said reagent is greater than about 9.0 and the relative Van Slyke buffer value $\beta'$ of said reagent is greater than 1.

2. A reagent for the determination of magnesium, comprising Calmagite and a strong buffer such that the pH of said reagent is greater than about 9.0 and the relative Van Slyke buffer value $\beta'$ of said reagent is between 2 and 20.

3. A reagent for the determination of magnesium, comprising Calmagite and a strong buffer such that the pH of said reagent is greater than about 9.0 and the relative Van Slyke buffer value $\beta'$ of said reagent is between 3 and 15.

4. A reagent according to any of claims 1, 2, or 3, in the absence of polyvinylpyrrolidone or any other substance to correct for spectral absorption differences due to the presence of protein.

5. A reagent according to any of claims 1, 2, or 3 further comprising a stabilizing agent selected from the group consisting of dimethylsulfoxide, a non-ionic surfactant, and a mixture of dimethylsulfoxide and a non-ionic surfactant.

6. A reagent according to claim 4, further comprising a stabilizing agent selected from the group consisting of dimethylsulfoxide, a non-ionic surfactant, and a mixture of dimethylsulfoxide and a non-ionic surfactant.

7. An assay for the determination of magnesium in a sample, comprising:
   (a) combining the sample, said sample being free from treatment for removal of any protein contained therein, with the reagent recited in any of claims 1, 2, or 3; and
   (b) measuring the absorbance of the magnesium-Calmagite complex thus formed.

8. An assay for the determination of magnesium in a sample, comprising:
   (a) combining the sample, said sample being free from treatment for removal of any protein contained therein, with the reagent recited in claim 4; and
   (b) measuring the absorbance of the magnesium-Calmagite complex thus formed.

9. An assay for the determination of magnesium in a sample, comprising:
   (a) combining the sample, said sample being free from treatment for removal of any protein contained therein, with the reagent recited in claim 5; and
   (b) measuring the absorbance of the magnesium-Calmagite complex thus formed.

10. An assay for the determination of magnesium in a sample, comprising:

(a) combining the sample, said sample being free from treatment for removal of any protein contained therein, with the reagent recited in claim 6; and (b) measuring the absorbance of the magnesium-Calmagite complex thus formed.

11. An assay for the determination of magnesium in a sample, comprising:
   (a) combining the sample, said sample being free from treatment for removal of any protein contained therein, with the reagent recited in any of claims 1, 2, or 3; and
   (b) measuring the loss in absorbance of the non-metallized Calmagite.

12. An assay for the determination of magnesium in a sample, comprising:
   (a) combining the sample, said sample being free from treatment for removal of any protein contained therein, with the reagent recited in claim 4; and
   (b) measuring the loss in absorbance of the non-metallized Calmagite.

13. An assay for the determination of magnesium in a sample, comprising:
   (a) combining the sample, said sample being free from treatment for removal of any protein contained therein, with the reagent recited in claim 5; and
   (b) measuring the loss in absorbance of the non-metallized Calmagite.

14. An assay for the determination of magnesium in a sample, comprising:
   (a) combining the sample, said sample being free from treatment for removal of any protein contained therein, with the reagent recited in claim 6; and
   (b) measuring the loss in absorbance of the non-metallized Calmagite.

15. A reagent for the determination of magnesium, comprising Eriochrome Black T and a strong buffer such that the pH of said reagent is greater than about 9.0 and the relative Van Slyke buffer value $\beta'$ of said reagent is greater than 1.

16. A reagent for the determination of magnesium, comprising Eriochrome Black T and a strong buffer such that the pH of said reagent is greater than about 9.0 and the relative Van Slyke buffer value $\beta'$ of said reagent is between 2 and 20.

17. A reagent for the determination of magnesium, comprising Eriochrome Black T and a strong buffer such that the pH of said reagent is greater than about 9.0 and the relative Van Slyke buffer valve $\beta'$ of said reagent is between 3 and 15.

18. A reagent according to any of claims 15, 16, or 17, in the absence of polyvinylpyrrolidone or any other substance to correct for spectral absorption differences due to the presence of protein.

19. A reagent according to any of claims 15, 16, or 17, further comprising a stabilizing agent selected from the group consisting of dimethylsulfoxide, a non-ionic surfactant, and a mixture of dimethylsulfoxide and a non-ionic surfactant.

20. A reagent according to claim 18, further comprising a stabilizing agent selected from the group consisting of dimethylsulfoxide, a non-ionic surfactant, and a mixture of dimethylsulfoxide and a non-ionic surfactant.

21. An assay for the determination of magnesium in a sample, comprising:
   (a) combining the sample, said sample being free from treatment for removal of any protein contained therein, with the reagent recited in any of claims 15, 16, or 17; and
   (b) measuring the absorbance of the magnesium-Eriochrome Black T complex thus formed.

22. An assay for the determination of magnesium in a sample, comprising:
   (a) combining the sample, said sample being free from treatment for removal of any protein contained therein, with the reagent recited in claim 18; and
   (b) measuring the absorbance of the magnesium-Eriochrome Black T complex thus formed.

23. An assay for the determination of magnesium in a sample, comprising:
   (a) combining the sample, said sample being free from treatment for removal of any protein contained therein, with the reagent recited in claim 19; and
   (b) measuring the absorbance of the magnesium-Eriochrome Black T complex thus formed.

24. An assay for the determination of magnesium in a sample, comprising:
   (a) combining the sample, said sample being free from treatment for removal of any protein contained therein, with the reagent recited in claim 20; and
   (b) measuring the absorbance of the magnesium-Eriochrome Black T complex thus formed.

25. An assay for the determination of magnesium in a sample, comprising:
   (a) combining the sample, said sample being free from treatment for removal of any protein contained therein, with the reagent recited in any of claims 15, 16, or 17; and
   (b) measuring the loss in absorbance of the non-metallized Eriochrome Black T.

26. An assay for the determination of magnesium in a sample, comprising:
   (a) combining the sample, said sample being free from treatment for removal of any protein contained therein, with the reagent recited in claim 18; and
   (b) measuring the loss in absorbance of the non-metallized Eriochrome Black T.

27. An assay for the determination of magnesium in a sample, comprising:
   (a) combining the sample, said sample being free from treatment for removal of any protein contained therein, with the reagent recited in claim 19; and
   (b) measuring the loss in absorbance of the non-metallized Eriochrome Black T.

28. An assay for the determination of magnesium in a sample, comprising:
   (a) combining the sample, said sample being free from treatment for removal of any protein contained therein, with the reagent recited in claim 20; and
   (b) measuring the loss in absorbance of the non-metallized Eriochrome Black T.

29. A reagent kit for the colorimetric determination of magnesium, said kit comprising:
   (a) a first reagent comprising a dye for binding magnesium, said dye selected from the group consisting of Calmagite and Eriochrome Black T; and
   (b) a second reagent comprising a strong buffer such that, when said second reagent is combined with said first reagent, the resulting reagent mixture has a pH of greater than about 9.0 and a relative Van Slyke buffer value $\beta'$ greater than 1.

30. A reagent kit for the colorimetric determination of magnesium, said kit comprising:
   a) a first reagent comprising a dye for binding magnesium, said dye selected from the group consisting of Calmagite and Eriochrome Black T; and (b) a second reagent comprising a strong buffer such that, when said second reagent is combined with said first reagent, the resulting reagent mixture has a pH of greater than about 9.0 and a relative Van Slyke buffer value $\beta'$ between 2 and 20.

31. A reagent kit for the colorimetric determination of magnesium, said kit comprising:
   (a) a first reagent comprising a dye for binding magnesium, said dye selected from the group consisting of Calmagite and Eriochrome Black T; and
   (b) a second reagent comprising a strong buffer such that, when said second reagent is combined with said first reagent, the resulting mixture has a pH of greater than about 9.0 and a relative Van Slyke buffer value $\beta'$ between 3 and 15.

32. A kit according to any of claims 29, 30, or 31, in which said reagents are in the absence of polyvinylpyrrolidone or any other substance to correct for spectral absorption differences due to the presence of protein.

33. A kit according to any of claims 29, 30, or 31, said first reagent further comprising a stabilizing agent selected from the group consisting of dimethylsulfoxide, a non-ionic surfactant, and a mixture of dimethylsulfoxide and a non-ionic surfactant.

34. A kit according to any of claims 29, 30, or 31, said second reagent further comprising a stabilizing agent selected from the group consisting of dimethylsulfoxide, a non-ionic surfactant, and a mixture of dimethylsulfoxide and a non-ionic surfactant.

35. A kit according to any of claims 29, 30, or 31, in which both reagents further comprise a stabilizing agent selected from the group consisting of dimethylsulfoxide, a non-ionic surfactant, and a mixture of dimethylsulfoxide and a non-ionic surfactant.

36. A stabilized reagent for the determination of magnesium, comprising:
   (a) a dye selected from the group consisting of Calmagite and Eriochrome Black T;
   (b) a buffer selected from the group consisting of monoethanolamine, diethanolamine, triethanolamine, diethylamine, 2-amino-2-methyl-1-propanol and 3-(cyclohexylamino)-propanesulfonic acid, such buffer being sufficient that the relative Van Slyke buffer value $\beta'$ of said reagent is between about 3 and 15; and
   (c) a stabilizing agent selected from the group consisting of dimethylsulfoxide, a non-ionic surfactant, and a mixture of dimethylsulfoxide and a non-ionic surfactant.

37. An assay for the determination of magnesium in a sample, comprising:
   (a) combining the sample, said sample being free from treatment for removal of any protein contained therein, with the reagent recited in claim 36; and
   (b) measuring the absorbance of the magnesium-dye complex thus formed.

38. An assay for the determination of magnesium in a sample, comprising:
   (a) combining the sample, said sample being free from treatment for removal of any protein contained therein, with the reagent recited in claim 36; and
   (b) measuring the loss in absorbance of the non-metallized dye.

* * * * *